(12) United States Patent
Frantsi et al.

(10) Patent No.: US 6,465,481 B1
(45) Date of Patent: Oct. 15, 2002

(54) BISPIDINE COMPOUNDS USEFUL IN THE TREATMENT OF CARDIAC ARRYTHMIAS

(75) Inventors: Marianne Frantsi, Kungsbacka; Kurt-Jürgen Hoffmann; Gert Strandlund, both of Kullavik, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/623,707

(22) PCT Filed: Jun. 15, 2000

(86) PCT No.: PCT/SE00/01251

§ 371 (c)(1),
(2), (4) Date: Sep. 7, 2000

(87) PCT Pub. No.: WO00/76997

PCT Pub. Date: Dec. 21, 2000

(30) Foreign Application Priority Data

Jun. 16, 1999 (SE) ................................. 9902271

(51) Int. Cl.$^7$ ........................ A61K 31/44; C07D 471/08
(52) U.S. Cl. .................... 514/300; 546/122; 546/18; 514/278
(58) Field of Search ................... 546/122, 18; 514/300, 514/278

(56) References Cited

U.S. PATENT DOCUMENTS 6,291,475 B1 * 9/2001 Alstermark et al. ........ 514/300

* cited by examiner

Primary Examiner—Bernard Dentz
(74) Attorney, Agent, or Firm—Nixon Vanderhye

(57) ABSTRACT

There is provided compounds of formula I,

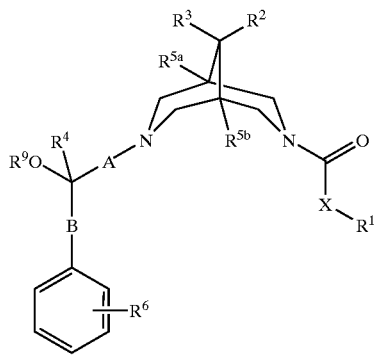

wherein $R^1$, $R^2$, $R^3$, $R^4$, $R^{5a}$, $R^{5b}$, $R^6$, $R^9$, X, A and B have meanings given in the description, which are useful in the prophylaxis and in the treatment of arrhythmias, in particular atrial and ventricular arrhythmias.

19 Claims, No Drawings

BISPIDINE COMPOUNDS USEFUL IN THE TREATMENT OF CARDIAC ARRYTHMIAS

This application is a 371 of PCT/SE00/01251 filed Jun. 15, 2000.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent application WO 91/07405, ye European patent applications 306 871, 308 843 and 655 228 and US Pat. Nos. 3,962,449, 4,556,662, 4,550,112, 4,459,301 and 5,468,858, as well as journal articles including inter alia J. Med. Chem. 39, 2559, (1996), Pharmacol. Res., 24, 149 (1991), Circulation, 90, 2032 (1994) and Anal. Sci. 9, 429, (1993). Known bispidine-based antiarrhythmic compounds include bisaramil (3-methyl-7-ethyl-9α, 4'-(Cl-benzoyloxy)-3,7-diazabicyclo[3.3.1]nonane), tedisamil (3', 7'-bis(cyclopropylmethyl)spiro-(cyclopentane-1,9')-3,7-diazabicyclo[3.3.1]nonane), SAZ-VII-22 (3-(4-chlorobenzoyl)-7-isopropyl-3,7-diazabicyclo[3.3.1] nonane), SAZ-VII-23 (3-benzoyl-7-isopropyl-3,7-diazabicyclo[3.3.1]nonane), GLG-V-13 (3-[4-(1H-imidazol-1-yl)benzoyl]-7-isopropyl-3,7-diazabicyclo[3.3.1]nonane), KMC-IV-84 (7-[4'-(1H-imidazol-1-yl)benzenesulfonyl]-3-isopropyl-3,7-diaza-bicyclo[3.3.1]nonane dihydroperchlorate and ambasilide (3-(4-aminobenzoyl)-7-benzyl-3,7-diazabicyclo[3.3.1]nonane).

We have surprisingly found that a novel group of bispidine-based compounds exhibit electrophysiological activity, preferably class III electrophysiological activity, and are therefore expected to be useful in the treatment of cardiac arrhythmias.

DISCLOSURE OF THE INVENTION

According to the invention there is provided compounds of formula I,

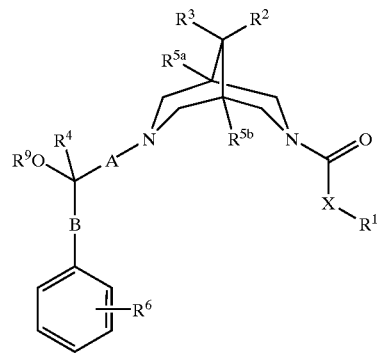

wherein $R^1$ represents $C_{1-12}$ alkyl, $-(CH_2)_a$-aryl, or $-(CH_2)_a$-$Het^1$ (all of which are optionally substituted and/or terminated (as appropriate) by one or more substituents selected from $-OH$, halo, cyano, nitro, $C_{1-4}$ alkyl and/or $C_{1-4}$ alkoxy);

a represents 0, 1, 2, 3, or 4;

$Het^1$ represents a five to ten-membered heterocyclic ring containing one or more heteroatoms selected from oxygen, nitrogen and/or sulfur, and which also optionally includes one or more =O sub stituents;

X represents O or S;

$R^{5a}$ and $R^{5b}$ independently represent H or $C_{1-3}$ alkyl;

$R^2$ and $R^3$ independently represent H, $C_{1-4}$ alkyl (optionally substituted and/or terminated with one or more nitro or cyano groups), $OR^7$, $N(R^{7a})R^{7b}$, $OC(O)$ RS or together form $-O-(CH_2)_2-O-$, $-(CH_2)_3-$, $-(CH_2)_4-$ or $-(CH_2)_5-$;

$R^7$ and $R^8$ independently represent H, $C_{1-6}$ alkyl or $-(CH_2)_b$-aryl (which latter two groups are optionally substituted and/or terminated by one or more substituents selected from $-OH$, halo, cyano, nitro, $C_{1-4}$ alkyl and/or $C_{1-4}$ alkoxy);

$R^{7a}$ and $R^{7b}$ independently represent H or $C_{1-6}$ alkyl;

b represents 0, 1, 2, 3 or 4;

$R^4$ represents H or $C_{1-6}$ alkyl;

$R^9$ represents $-C(O)R^{10}$, $C_{1-6}$ alkyl, $-(CH_2)_d$-aryl or $-(CH_2)_d$-$Het^2$ (which latter three groups are optionally substituted by one or more substituents selected from $-OH$, halo, cyano, nitro, $C_{1-4}$ alkyl, $C_{1-4}$ alkoxy, $C(O)R^{11}$, $C(O)OR^{12}$ and/or $-N(H)S(O)_eR^{13}$);

$R^{10}$, $R^{11}$ and $R^{12}$ independently represent H, $C_{1-6}$, alkyl, $Het^3$ or $-(CH_2)_f$-aryl (which latter three groups are optionally substituted and/or terminated (as appropriate) by one or more substituents selected from $-OH$, cyano, halo, amino, nitro, $C_{1-6}$, alkyl, $C_{1-6}$ alkoxy, $C(O)R^{14}$, $C(O)OR^{15}$ and/or $N(H)S(O)_2R^{16}$);

$R^{13}$ represents $C_{1-6}$ alkyl or $-(CH_2)_g$-aryl (both of which are optionally substituted and/or terminated (as appropriate) by one or more substituents selected from halo, nitro, $C_{1-6}$ alkyl and/or $C_{1-6}$ alkoxy);

$R^{14}$ and $R^{15}$ independently represent H, $C_{1-6}$ alkyl or aryl;

$R^{16}$ represents $C_{1-6}$ alkyl or aryl;

e represents 0, 1 or 2;

d, f and g independently represent 0, 1, 2, 3 or 4;

$Het^2$ and $Het^3$ independently represent five to ten-membered heterocyclic rings containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_{1-6}$ alkyl (optionally terminated by $N(H)C(O)OR^{18a}$), $C_{1-6}$ alkoxy, —C(O)N(H)$R^{19}$, —NHC(O)N(H)$R^{20}$, —N(H)S(O)$_2R^{21}$ and/or —OS(O)$_2R^{22}$;

$R^{19}$ and $R^{20}$ independently represent H or $C_{1-6}$ alkyl;

$R^{18a}$, $R^{21}$ and $R^{22}$ independently represent $C_{1-6}$ alkyl;

A represents a single bond, $C_{1-6}$ alkylene or —(CH$_2$)$_j$C(H)(OR$^{23}$)(CH$_2$)$_k$— (in which latter group, the —(CH$_2$)$_j$— group is attached to the bispidine nitrogen atom and which latter two groups are optionally substituted by one or more —OH groups);

B represents a single bond, $C_{1-4}$ alkylene, —(CH$_2$)$_m$N(R$^{24}$)—, —(CH$_2$)$_m$S(O)$_n$—, —(CH$_2$)$_m$O— (in which three latter groups, the —(CH$_2$)$_m$— group is attached to the carbon atom bearing OR$^9$ and R$^4$), —C(O)N(R$^{24}$)— (in which latter group, the —C(O)— group is attached to the carbon atom bearing OR$^9$ and R$^4$), —N(R$^{24}$)C(O)O(CH$_2$)$_m$— or —N(R$^{24}$)(CH$_2$)$_m$— (in which latter two groups, the N(R$^{24}$) group is attached to the carbon atom bearing OR$^9$ and R$^4$);

j represents 1, 2, 3 or 4;

k and m independently represent 0, 1, 2, 3 or 4;

n represents 0, 1 or 2;

$R^{23}$ represents H, $C_{1-6}$ alkyl or C(O)R$^{25}$;

$R^{24}$ represents H or $C_{1-6}$ alkyl;

$R^{25}$ represents H, $C_{1-6}$ alkyl, Het$^4$ or —(CH$_2$)$_p$-aryl (which latter two groups are optionally substituted and/or terminated (as appropriate) by one or more substituents selected from —OH, cyano, halo, amino, nitro, $C_{1-6}$ alkyl and/or $C_{1-6}$ alkoxy);

Het$^4$ represents a five to ten-membered heterocyclic ring containing one or more heteroatoms selected from oxygen, nitrogen and/or sulfur, and which also optionally includes one or more =O substituents;

p represents 0, 1, 2, 3 or 4;

or a pharmaceutically acceptable derivative thereof;

provided that m does not represent 0 when B represents —(CH$_2$)$_m$N(R$^{24}$), —(CH$_2$)$_m$S(O)$_n$— or —(CH$_2$)$_m$O—, which compounds are referred to hereinafter as "the compounds of the invention".

Aryl groups that may be mentioned include $C_{6-10}$ aryl groups, such as phenyl, naphthyl and the like. Oxyaryl groups that may be mentioned include $C_{6-10}$ oxyaryl groups, such as oxyphenyl (phenoxy), oxynaphthyl (naphthoxy) and the like. When substituted, aryl and aryloxy groups are preferably substituted by between one and three substituents.

Het$^1$, Het$^2$, Het$^3$ and Het$^4$ groups that may be mentioned include those containing 1 to 4 heteroatoms (selected from the group oxygen, nitrogen and/or sulfur) and in which the total number of atoms in the ring system is between five and ten. Het (Het$^1$, Het$^2$, Het$^3$ and Het$^4$) groups may be wholly/partly aromatic in character and may be bicyclic and/or include one or more =O substituents. Heterocyclic groups that may be mentioned include morpholinyl, thiazolyl, oxazolyl, isoxazolyl, cinnolinyl, quinazolinyl, phthalazinyl, purinyl, benzimidazolyl, pyrimindinyl, piperazinyl, pyrazinyl, piperidinyl, pyridinyl, pyrrolinyl, pyrrolidinyl, pyrollidinonyl, triazolyl, imidazolyl, quinolinyl, isoquinolinyl, dioxanyl, benzodioxanyl, benzodioxolyl, benzodioxepanyl, benzomorpholinyl, indolyl, pyrazolyl, pyrrolyl, benzothiophenyl, thiophenyl, chromanyl, thiochromanyl, benzofuranyl, pyranyl, tetrahydropyranyl, tetrahydrofuranyl, furanyl and the like. Values of Het$^2$ that may be mentioned include pyridinyl. Values of Het$^3$ that may be mentioned include piperazinyl (which latter group is optionally substituted by one or more C(O)R$^{14}$ and/or C(O)OR$^{15}$ group). Substituents on Het (Het$^1$, Het$^2$, Het$^3$ and Het$^4$) groups may, where appropriate, be located on any atom in the ring system including a heteroatom. The point of attachment of Het (Het$^1$, Het$^2$, Het$^3$ and Het$^4$) groups may be via any atom in the ring system including (where appropriate) a heteroatom. Het may optionally be in the N- or S-oxidised form.

Pharmaceutically acceptable derivatives include salts and solvates. Salts which may be mentioned include acid addition salts. Pharmaceutically acceptable derivatives also include $C_{1-4}$ alkyl quaternary ammonium salts and N-oxides, provided that, when a N-oxide is present:

(a) no Het (Het$^1$, Het$^2$, Het$^3$, Het$^4$) groups contain an unoxidised S-atom;

(b) X does not represent S; (c) n does not represent 0, when B represents —(CH$_2$)$_m$S(O)$_n$—; and/or (d) e does not represent 0, when R$^9$ is substituted by —N(H)S(O)$_e$R$^{13}$.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Alkyl groups that $R^1$, $R^2$, $R^3$, $R^4$, $R^{5a}$, $R^{5b}$, $R^6$, $R^7$, $R^{7a}$, $R^{7b}$, $R^8$, $R^9$, $R^{10}$, $R^{11}$, $R^{12}$, $R^{13}$, $R^{14}$, $R^{15}$, $R^{16}$, $R^{18a}$, $R^{19}$, $R^{20}$, $R^{21}$, $R^{22}$, $R^{23}$, $R^{24}$ and $R^{25}$ may represent, and with which $R^1$, $R^7$, $R^8$, $R^9$, $R^{10}$, $R^{11}$, $R^{12}$, $R^{13}$ and $R^{25}$ may be substituted; and alkoxy groups that $R^6$ may represent, and with which $R^1$, $R^7$, $R^8$, $R^9$, $R^{10}$, $R^{11}$, $R^{12}$, $R^{13}$ and $R^{25}$ may be substituted, may be linear or, when there is a sufficient number (i.e. three) of carbon atoms, be branched and/or cyclic. Further, when there is a sufficient number (i.e. four) of carbon atoms, such alkyl and alkoxy groups may also be part cyclic/acyclic. Such alkyl and alkoxy groups may also be saturated or, when there is a sufficient number (i.e. two) of carbon atoms, be unsaturated and/or interrupted by oxygen and/or substituted by one or more fluoro groups.

Alkylene groups that A and B may represent, and —(CH$_2$)— containing groups that $R^1$, $R^2$ and $R^3$ (together), $R^7$, $R^8$, $R^9$, $R^{10}$, $R^{11}$, $R^{12}$, $R^{13}$, $R^{25}$, A and B may include, may be linear or, when there is a sufficient number (i.e. two) of carbon atoms, be branched. Such alkylene groups and —(CH$_2$)— containing chains may also be saturated or, when there is a sufficient number (i.e. two) of carbon atoms, be unsaturated and/or interrupted by oxygen.

As used herein, the term "halo" includes fluoro, chloro, bromo or iodo.

Abbreviations are listed at the end of this specification.

According to a further aspect of the invention there is provided compounds of formula I as hereinbefore defined, except that B does not represent —N(R$^{24}$)C(O)O(CH$_2$)$_m$— or —N(R$^{24}$)(CH$_2$)$_m$—.

Preferred compounds of the invention include those in which:

- $R^1$ represents optionally substituted —(CH$_2$)$_a$-phenyl, in which a is 0, 1, 2 or 3, or, preferably, optionally substituted, optionally unsaturated, linear, branched or cyclic, $C_{1-8}$ alkyl (which latter group may also be interrupted by an oxygen atom);
- $R^2$ represents H;
- $R^3$ represents H;
- $R^4$ represents H or $C_{1-2}$ alkyl; $R^{5a}$ and $R^{5b}$ either both represent H or both represent methyl;
- $R^6$ represents one or more substituents selected from $C_{1-6}$alkyl, cyano, nitro, amino, C(O)N(H)R$^{19}$ and/or —N(H)S(O)$_2$R$^{21}$;
- X represents O;
- A represents a single bond or linear, or branched, $C_{1-6}$ alkylene (which group is also optionally interrupted by O);
- B represents a single bond, $C_{1-4}$ alkylene, —(CH$_2$)$_m$O— or —(CH$_2$)$_m$N(R$^{24}$)— (in which latter two cases m is 1, 2 or 3);
- $R^9$ represents C(O)R$^{10}$ (in which R$^{10}$ represents $C_{1-3}$ alkyl or optionally substituted Het$^3$); $C_{13}$ alkyl; optionally substituted phenyl; or optionally substituted —(CH$_2$)$_d$-Het$^2$ (in which d is 0, 1 or 2);
- when the bispidine nitrogen bearing A optionally bears a $C_{1-4}$ alkyl group, thus forming a quaternary ammonium salt, the alkyl group is a methyl group.

More preferred compounds of the invention include those in which:

- $R^1$ represents linear or branched $C_2$alkyl;
- $R^4$ represents H;
- $R^{5a}$ and $R^{5b}$ both represent H;
- $R^6$ represents cyano, preferably in the para position relative to B;
- A represents Cl$_4$ alkylene;
- B represents a single bond;
- $R^9$ represents C(O)R$^{10}$ (in which R$^{10}$ represents $C_{1-2}$ alkyl or 1,4-piperazinyl (optionally substituted in the 4-position by a C(O)R$^{14}$ or a C(O)OR$^{15}$ group)); $C_{1-2}$ alkyl; phenyl (optionally substituted by one or more groups selected from $C_{1-2}$ alkoxy, OH, halo and/or N(H)S(O)$_2$R$^{13}$ (in which R$^{13}$ is $C_{1-2}$ alkyl); or —(CH$_2$)$_d$-Het$^2$ (in which d represent 0 or 1 and Het$^2$ represents pyridinyl, optionally in the form of an N-oxide).

Preferred compounds of the invention include the compounds of Examples described hereinafter.

Preparation

According to the invention there is also provided a process for the preparation of compounds of formula I which comprises:

(a) reaction of a compound of formula II,

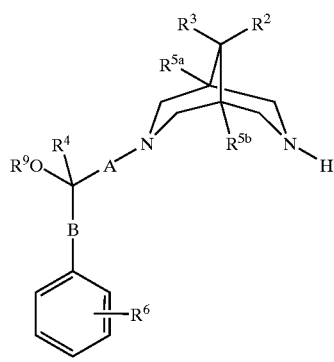

wherein $R^2$, $R^3$, $R^4$, $R^{5a}$, $R^{5b}$, $R^6$, $R^9$, A and B are as hereinbefore defined with a compound of formula III,

R$^1$XC(O)L$^1$   III wherein $L^1$ represents a leaving group, such as Hal, imidazolyl or —OC(O)XR$^1$, Hal represents Cl, Br or I, and $R^1$ and X are as hereinbefore defined, for example at or above room temperature in the presence of a suitable base (e.g. aqueous. NaOH, K$_2$CO$_3$ or triethylamine) and an appropriate organic solvent (e.g. CH$_2$Cl$_2$, THF, acetonitrile, toluene, or mixtures of such solvents);

(b) reaction of a compound of formula IV

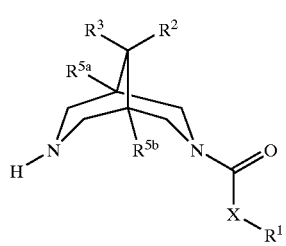

wherein $R^1$, $R^2$, $R^3$, $R^{5a}$, $R^{5b}$ and X are as hereinbefore defined, with a compound of formula V,

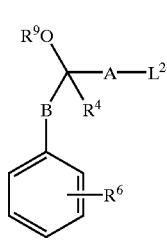

wherein $L^2$ represents a leaving group (e.g. mesylate, tosylate or Hal, where Hal is as hereinbefore defined) and $R^4$, $R^6$, $R^9$, A and B are as hereinbefore defined, for example at elevated temperature (e.g. between 35° C. and reflux temperature) in the presence of a suitable base (e.g. triethylamine or K$_2$CO$_3$) and an appropriate organic solvent (e.g. acetonitrile or dimethylsulfoxide);

(c) for compounds of formula I in which $R^2$ and $R^3$ both represent H, reduction of a corresponding compound of formula VI,

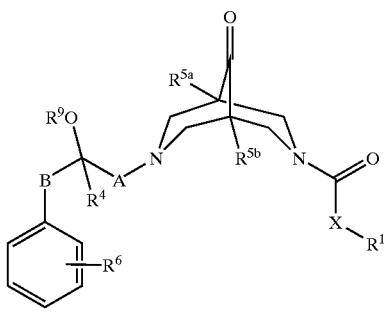

VI wherein $R^1$, $R^4$, $R^{5a}$, $R^{5b}$, $R^6$, $R^9$, A, B and X are as hereinbefore defined, and in which the bridgehead C=O group may be activated using an appropriate agent, such as tosylhydrazine, in the presence of a suitable reducing agent (e.g. sodium borohydride or sodium cyanoborohydride) and an appropriate organic solvent (e.g. a lower alkyl alcohol); when the C=O group is activated, the activation step may be carried out at between room and reflux temperature in the presence of an appropriate organic solvent (e.g. a lower alkyl alcohol such as methanol, ethanol or IPA), whereafter the reducing agent may be added to the reaction mixture and the reduction carried out at between 60° C. and reflux, advantageously in the presence of a suitable organic acid (e.g. acetic acid);

(d) for compounds of formula I in which one or $R^2$ and $R^3$ represents H and the other represents —OH, reduction of a corresponding compound of formula VI, as hereinbefore defined, in the presence of a mild reducing agent, e.g. sodium borohydride, and an appropriate organic solvent (e.g. a lower alcohol such as methanol or ethanol);

(d) for compounds of formula I in which one or $R^2$ and $R^3$ represents H and the other represents —OH, reduction of a corresponding compound of formula VI, as hereinbefore defined, in the presence of a mild reducing agent, e.g. sodium borohydride, and an appropriate organic solvent (e.g. a lower alcohol such as methanol or ethanol);

(e) for compounds of formula I in which $R^9$ represents optionally substituted $C_{1-6}$ alkyl, optionally substituted —$(CH_2)_d$-aryl or optionally substituted —$(CH_2)_d$-$Het^2$, reaction of a compound of formula VII,

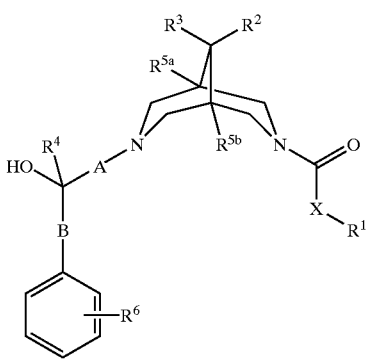

VII wherein $R^1$, $R^2$, $R^3$, $R^4$, $R^{5a}$, $R^{5b}$, $R^6$, A, B and X are as hereinbefore defined with a compound of formula VIII, $R^{9a}OH$      VIII wherein $R^{9a}$ represents optionally substituted $C_{1-6}$alkyl, optionally substituted —$(CH_2)_d$-aryl or optionally substituted —$(CH2)_d$-HeO, wherein d and $Het^2$ are as hereinbefore defined, for example at between ambient (e.g. 25° C.) and reflux temperature, under Mitsunobu-type conditions (i.e. in the presence of e.g. triphenylphosphine, an azodicarboxylate derivative (e.g. 1,1'-(azodicarbonyl)dipiperidine) and a suitable organic solvent (e.g. dichloromethane));

(f) for compounds of formula I in which $R^9$ represents optionally substituted $C_{1-6}$ alkyl, optionally substituted —$(CH_2)_d$-aryl or optionally substituted —$(CH_2)_d$-$Het^2$, reaction of a compound of formula IX,

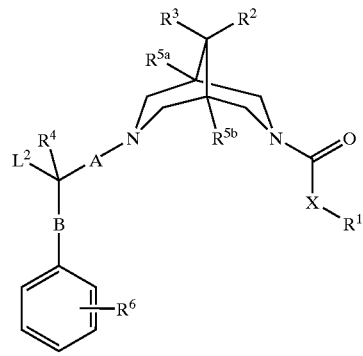

IX wherein $L^2$, $R^1$, $R^2$, $R^3$, $R^4$, $R^{5a}$, $R^{5b}$, $R^6$, A, B and X are as hereinbefore defined with a compound of formula VIII as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or DMF));

(g) for compounds of formula I in which $R^9$ represents $C(O)R^{10}$ and $R^{10}$ is as hereinbefore defined, reaction of a corresponding compound of formula VII as hereinbefore defined and a compound of formula X, $R^{10}CO_2H$      X wherein $R^{10}$ is as hereinbefore defined, for example at ambient temperature i (e.g. 25° C.) in the presence of a suitable coupling agent (e.g. 1-(3-dimethylaminopropyl)-3-ethylcarbodiimide), an appropriate catalyst (e.g. 4-dimethylaminopyridine) and a reaction-inert organic solvent (e.g. THF);

(h) for compounds of formula I in which $R^2$ and/or $R^3$ represent $OC(O)R^8$ and $R^8$ is as hereinbefore defined, coupling of a corresponding compound of formula I in which $R^2$ and/or $R^3$ (as appropriate) represents OH and a compound of formula XI, $R^8CO_2H$      XI wherein $R^8$ is as hereinbefore defined, for example at ambient temperature (e.g. 25° C.) in the presence of a suitable coupling agent (e.g. 1-(3-dimethylaminopropyl)-3-ethylcarbodiimide), an appropriate catalyst (e.g. 4-dimethylaminopyridine) and a reaction-inert organic solvent (e.g. THF);

(i) for compounds of formula I which are bispidine-nitrogen N-oxide derivatives, oxidation of the corresponding bispidine nitrogen of a corresponding compound of formula I, in the presence of a suitable oxidising agent (e.g. m-chloroperbenzoic acid), for example at 0° C. in the presence of a suitable organic solvent (e.g. DCM);

(j) for compounds of formula I which are $C_{1-4}$ alkyl quaternary ammonium salt derivatives, in which the alkyl group is attached to a bispidine nitrogen, reaction, at the bispidine nitrogen, of a corresponding compound of formula I with a compound of formula XII, $$R^xHal \qquad \text{XII}$$

wherein $R^x$ represents $C_{1-4}$ alkyl and Hal is as hereinbefore defined, for example at room temperature in the presence of an appropriate organic solvent (e.g. DMF), followed by purification (using e.g. HPLC) in the presence of a suitable counter-ion provider (e.g. $NH_4OAc$);

(k) reaction of a compound of formula II, as hereinbefore defined, with a compound of formula XIII, $$R^1XH \qquad \text{XIII}$$

wherein $R^1$ and X are as hereinbefore defined, in the presence of 1,1'-carbonyldiimidazole, for example by refluxing in the presence of a suitable organic solvent (e.g. THF); or (l) for compounds of formula I in which one or both of $R^2$ and $R^3$ represent —$N(R^{7a})R^{7b}$ in which one or both or $R^{7a}$ and $R^{7b}$ represents $C_{1-6}$ alkyl, alkylation of a corresponding compound of formula I in which $R^2$ and/or $R^3$ represent —$N(R^{7a})R^{7b}$ (as appropriate) in which $R^{7a}$ and/or $R^{7b}$ (as appropriate) represent H, using a compound of formula XIIIA, $$R^{7c}L^1 \qquad \text{XIIIA}$$

wherein $R^{7c}$ represents $C_{1-6}$ alkyl and $L^1$ is as hereinbefore defined, for example under conditions that are well known to those skilled in the art; or (m) conversion of one $R^6$ substituent to another using techniques well known to those skilled in the art.

Compounds of formula II may be prepared by reaction of a compound of formula XIV,

XIV wherein $R^2$, $R^3$, $R^{5a}$ and $R^{5b}$ are as hereinbefore defined, with a compound of formula V as hereinbefore defined, for example as described hereinbefore for synthesis of compounds of formula I (process step (b)).

Compounds of formula II in which $R^2$ and $R^3$ both represent H may be prepared by reduction of a compound of formula XV,

XV wherein $R^4$, $R^{5a}$, $R^{5b}$, $R^6$, $R^9$, A and B are as hereinbefore defined, and in which the C=O group may be activated using an appropriate agent, such as tosylhydrazine, for example as described hereinbefore for synthesis of compounds of formula I (process step (c)).

Compounds of formula II in which $R^2$ represents OH and $R^3$ represents optionally substituted $C_{1-4}$ alkyl, may be prepared by reaction of a compound of formula XV, or a protected derivative thereof, with a compound of formula XVI, $$R^{3a}MgHal \qquad \text{XVI}$$

wherein $R^{31}$ represents $C_{1-4}$ alkyl (optionally substituted and/or terminated with one or more cyano groups) and Hal is as hereinbefore defined, for example at between −25° C. and ambient temperature in the presence of a suitable solvent (e.g. diethyl ether).

Compounds of formula IV may be prepared by reaction of a compound of formula XIV, as hereinbefore defined, with a compound of formula III as hereinbefore defined, for example as described hereinbefore for synthesis of compounds of formula I (process step (a)).

Compounds of formula IV may alternatively be prepared by reaction of a compound of formula XIV, as hereinbefore defined, with a compound of formula XIII, as hereinbefore defined, in the presence of 1,1'-carbonyldiimidazole, for example as described hereinbefore for synthesis of compounds of formula I (process step (k)).

Compounds of formula IV in which $R^2$ and $R^3$ represent H may alternatively be prepared by reduction of a corresponding compound of formula XVII,

XVII wherein $R^1$, $R^{5a}$, $R^{5b}$ and X are as hereinbefore defined, and in which the bridgehead C=O group may be activated using an appropriate agent, such as tosylhydrazine, for example as described hereinbefore for compounds of formula I (process step (c)).

Compounds of formula V may be prepared by standard techniques. For example compounds of formula V in which:

(1) B represents —$(CH_2)_mO$— may be prepared by coupling a compound of formula XVIII,

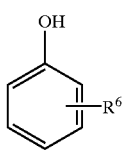

XVIII wherein $R^6$ is as hereinbefore defined, to a compound of formula XIX,

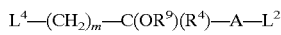

L$^4$—(CH$_2$)$_m$—C(OR$^9$)(R$^4$)—A—L$^2$    XIX wherein $L^4$ represents a suitable leaving group (e.g. Hal) and Hal, m, $R^4$, $R^9$, A and $L^2$ are as hereinbefore defined;

(2) B represents —C(O)N(R$^{24}$)— may be prepared by coupling a compound of formula XX,

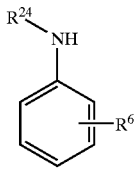

XX wherein $R^6$ and $R^{24}$ are as hereinbefore defined, to a compound of formula XXI,

L$^4$—C(O)—C(OR$^9$)(R$^4$)—A—L$^2$    XXI wherein $L^4$, $R^4$, $R^9$, A and $L^2$ are as hereinbefore defined;

in both cases, under conditions which are well known to those skilled in the art.

Compounds of formula V in which A represents $C_2$-alkylene and $R^9$ represents optionally substituted $C_{1-6}$ alkyl, optionally substituted —(CH$_2$)$_d$— aryl or optionally substituted —(CH$_2$)$_d$-Het$^2$ may alternatively be prepared by reaction of a compound of formula VIII as hereinbefore defined with a compound of formula XXII,

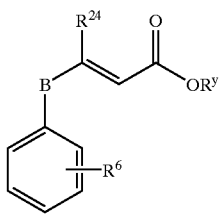

XXII wherein $R^y$ represents $C_{1-4}$ alkyl or aryl (which two groups are optionally substituted with one or more substituents selected from $C_{1-4}$ alkyl or halo) and $R^4$, $R^6$ and B are as hereinbefore defined, for example at between ambient temperature (e.g. 25° C.) and reflux temperature in the presence of a suitable base (e.g. $K_2CO_3$) and an appropriate organic solvent (e.g. acetonitrile), followed by conversion of the ester functionality to an $L^2$ group (in which $L^2$ is as hereinbefore defined), under conditions that are well known to those skilled in the art.

Compounds of formula V in which B represents —(CH$_2$)$_m$S(O)— or —(CH$_2$)$_m$S(O)$_2$— may be prepared by oxidation of a corresponding compound of formula V wherein B represents —(CH$_2$)$_m$S—, wherein m is as hereinbefore defined, in the presence of an appropriate amount of a suitable oxidising agent (e.g. m-chloroperbenzoic acid) and an appropriate organic solvent.

Compounds of formula VII may be prepared in a similar fashion to compounds of formula I (see, for example, process steps (a) or (b)).

Compounds of formula IX may be prepared by replacement of the OH group of a compound of formula VII with an $L^2$ group under conditions that are well known to those skilled in the art.

Compounds of formula XIV in which $R^2$ and $R^3$ both represent H may be prepared by reduction of a compound of formula XXIII,

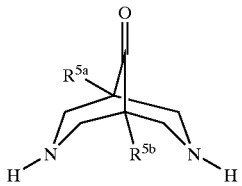

XXIII wherein $R^{5a}$ and $R^{5b}$ are as hereinbefore defined, under appropriate conditions (for example conditions such as those described in respect of the preparation of compounds of formula I (process step (c))).

Compounds of formula XIV in which $R^2$ represents OH and $R^3$ does not represent H, may be prepared by reaction of a corresponding compound of formula XXIII as hereinbefore defined, with a compound of formula XVI as hereinbefore defined, under appropriate conditions (for example conditions such as those described hereinbefore for the production of compounds of formula II in which $R^2$ represents OH and $R^3$ represents $R^{3a}$).

Compounds of formula XIV in which $R^2$ and $R^3$ together represent —O—(CH$_2$)$_2$—O—, —(CH$_2$)$_3$—, —(CH$_2$)$_4$— or —(CH$_2$)$_5$— may be prepared by reduction of a compound of formula XXIV

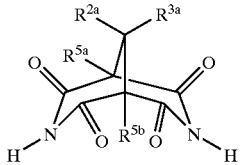

XXIV wherein $R^{2a}$ and $R^{3a}$ together represent —O—(CH$_2$)$_2$—O—, —(CH$_2$)$_3$—, —(CH$_2$)$_4$— or —(CH$_2$)$_5$— and $R^{5a}$ and $R^{5b}$ are as hereinbefore defined in the presence of a suitable reducing agent (e.g. LiAlH$_4$) under conditions that are well known to those skilled in the art.

Compounds of formulae VI, XV, XVII and XXIII may be prepared, advantageously, by reaction of a compound of formula XXV,

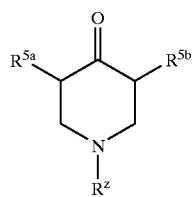

XXV wherein $R^z$ represents H or —C(O)XR$^1$ and $R^1$, $R^{5a}$, $R^{5b}$ and X are as hereinbefore defined, or a protected derivative thereof, with (as appropriate) either (1) a compound of formula XXVI,

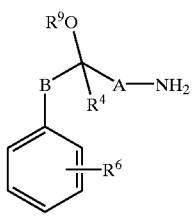

or a protected derivative thereof, wherein $R^4$, $R^6$, $R^9$, A and B are as hereinbefore defined, or (2) $NH_3$ (or a protected (e.g. benzyl) derivative thereof), in all cases in the presence of a formaldehyde (i.e. an appropriate source of formaldehyde, such as paraformaldehyde or formalin solution).

The formation of compounds of formulae VI, XV, XVII and XXIII may be carried out in this way for example at between room temperature and reflux (depending upon the concentration of the reactants) in the presence of an appropriate solvent (e.g. ethanol or methanol) and, preferably, in the presence of an organic acid (e.g. a $C_{1-6}$ carboxylic acid, especially acetic acid).

Compounds of formula XXIV may be prepared in accordance with techniques which are well known to those skilled in the art. For example, compounds of formula XXIV in which $R^{2a}$ and $R^{3a}$ together represent —$(CH_2)_3$—, —$(CH_2)_4$— or —$(CH_2)_5$— and $R^{5a}$ and $R^{5b}$ are both H may be prepared by reaction of a compound of formula XXVII,

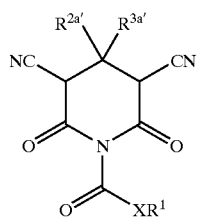

wherein $R^{2a}$ and $R^{3a}$ together represent —$(CH_2)_3$—, —$(CH_2)_4$— or —$(CH_2)_5$—, and X, $R^1$, $R^{5a}$ and $R^{5b}$ are as hereinbefore defined with a mixture of phosphoric acid and sulfuric acid, for example at 120° C.

Compounds of formulae III, VIII, X, XI, XII, XIII, XIIIA, XVI, XVIII, XIX, XX, XXI, XXII, XXV, XXVI and XXVII, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other substituents using techniques well known to those skilled in the art. For example, nitrobenzene may be reduced to an aminobenzene, hydroxy may be converted to alkoxy, alkoxy may be hydrolysed to hydroxy etc.

The compounds of the invention may be isolated from their reaction mixtures using conventional techniques.

It will be appreciated by those skilled in the art that, in the processes described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyloxy groups (e.g. methyl- and ethylcarbonyloxy groups). Suitable protecting groups for amino include benzyl, tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided: (a) a compound of formula II as hereinbefore defined or a protected derivative thereof; (b) a compound of formula IV as hereinbefore defined, or a protected derivative thereof, provided that when $R^{5a}$ and $R^{5b}$ both represent H, then at least one of $R^2$ and $R^3$ represents $OR^7$, $OC(O)R^8$ or $C_{1-4}$ alkyl, which alkyl group is substituted and/or terminated with one or more nitro or cyano group; (c) a compound of formula VI, as hereinbefore defined, or a protected derivative thereof; (d) a compound of formula XV, as hereinbefore defined, or a protected derivative thereof.

Medical and Pharmaceutical use

The compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class III activity. Although compounds of the invention have been found to exhibit class III activity in particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base, a pharmaceutically acceptable ion exchanger or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.05 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I, class II and/or class IV activity in addition to class III activity)) than, be more potent than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects In Anaesthetised Guinea Pigs

Guinea pigs weighing between 660 an 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph ink-jet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, Comput. Methods Programs Biomed. 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacing was started and a new recording was made. Five minutes after the previous dose, the next dose of test substance was administered. Six to ten consecutive doses were given during each experiment.

Data analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS), a Hewlett Packard model 6890 gas chromatograph connected to a Hewlett-Packard model 5973A mass spectrometer via a Hewlett Packard HP-5-MS GC column, or a Shimadzu QP-5000 GC/mass spectrometer (CI, methane). $^1$H NMR and $^{13}$C NMR measurements were performed on a BRUKER ACP 300 and Varian UNITY plus 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Example 1 tert-Butyl 7-[4-(4-Cyanophenyl)-4-(3,4-dimethoxyphenoxy)buty)]-3,7-di-azabicyclo[3.3.1] nonane-3-carboxylate (i) 3,7-Dibenzyl-3,7-diazabicyclo[3.3.1]nonane-9-one The sub-title compound was prepared according to the procedure described in J. Org. Chem., 41(9), 1976, pp. 1593–1597.

(ii) 3,7-Dibenzyl-3,7-diazabicyclo[3.3.1]nonane

The sub-title compound was prepared according to the procedure described in J. Org. Chem., 41(9), 1976, pp. 1593–1597, using 3,7-dibenzyl-3,7-diazabicyclo[3.3.1] nonane-9-one (from step (i) above) in place of N-benzyl-N'-methylbispidone.

(iii) 3-Benzyl-3,7-diazabicyclo[3.3.1]nonane

A solution of 3,7-dibenzyl-3,7-diazabicyclo[3.3.1]nonane (from step (ii) above; 97 g; 6.4 mmol) in aqueous ethanol (95%) was hydrogenated over 5% Pd/C at 1 atm. until tlc indicated that the reaction was complete. The catalyst was removed by filtration through a pad of Celite®, and the filtrate concentrated under reduced pressure to give the sub-title compound in quantitative yield.

$^{13}$C NMR in CDCl$_3$: δ 30.1, 33.4, 36.0, 52.5, 59.6, 64.3, 126.9, 128.3, 128.7, 138.8

(iv) tert-Butyl 7-benzyl-3,7-diazabicyclo[3.3.1]nonane-3-carboxylate

Di-tert-butyl dicarbonate was added slowly to a solution of 3-benzyl-3,7-diazabicyclo[3.3.1]nonane (from step (iii) above; 60 g; 277 mmol) in THF (600 mL). The reaction was stirred at rt until all of the starting material had been consumed (as indicated by tlc). The solvent was then removed under reduced pressure to give a quantitative yield of the sub-title compound.

(v) tert-Butyl 3,7-diazabicyclo[3.3.1]nonane-3-carboxylate

The sub-title compound was prepared in quantitative yield according to the procedure described in step (iii) above, using tert-butyl 7-benzyl-3,7-diazabicyclo[3.3.1]nonane-3-carboxylate (from step (iv) above) in place of 3,7-dibenzyl-3,7-diazabicyclo[3.3.1]nonane.

$^{13}$C NMR in CDCl$_3$: δ 28.05, 28.29, 31.33, 48.35, 49.11, 51.53, 79.34, 155.16

(vi) 4-(1-{[1-(tert-Butyl)-1,1-dimethylsilyl]oxy}-3-butenyl) benzonitrile

Imidazole (11.5 g; 170 mmol) and tert-butyldimethylsilyl chloride (12 g; 80 mmol) were added to a stirred solution of 1-(p-cyanophenyl)-3-buten-1-ol (11.5 g; 87 mmol) in DMF (50 mL), and the reaction mixture was stirred under an inert atmosphere ($N_2$) for 10 h. The solvent was then evaporated and the residue partitioned between water and diethyl ether. The organic layer was separated, dried, concentrated and subjected to column chromatography ($CH_2Cl_2$) to give the sub-title compound in a 86% yield.

(vii) 4-(1-{[1-(tert-Butyl)-1,1-dimethylsilyl]oxy}-4-hydroxybutyl)benzonitrile

Borane-methyl sulfide complex (13 mL; 2 M; 26 mmol) was added to a cooled (0° C.), stirred solution of 4-(1-{[1-(tert-butyl)-1,1-dimethylsilyl]oxy}-3-butenyl)benzonitrile (from step (vi) above; 15.2 g; 53 mmol) in THF (100 mL). After addition was complete, the reaction was allowed to warm to rt, and stirring was continued until all of the starting material was consumed (as indicated by tlc). The temperature was then lowered to 0° C. again, and an aqueous solution of sodium perborate tetrahydrate (19 g; 123 mmol in 55 mL) was added. The reaction mixture was stirred for a further 12 h at rt before brine (100 mL) and diethyl ether (150 mL) were added. The organic layer was then separated, dried, concentrated and subjected to column chromatography (hexane:EtOAc; 1:1) to give the title compound in 85% yield.

(viii) 4–1{[1-(tert-Butyl)-1,1-dimethylsilyl]oxy}-4-(4-cyanophenyl)butyl Methanesulfonate Methanesulfonyl chloride (7.9 g; 69 mmol) and triethylamine (10.3 g; 102 mmol) were added to a cooled (0° C.), stirred solution of 4-(1-{[1-(tert-butyl)-1,1-dimethylsilyl] oxy}-4-hydroxybutyl)benzonitrile (from step (vii) above; 20.8 g; 69 mmol) in $CH_2Cl_2$ (200 mL). The reaction was allowed to warm to rt until all of the starting material was consumed (as indicated by tlc). Water (200 mL) was added and the organic layer was separated, dried and concentrated to give the title compound in 98% yield.

(ix) tert-Butyl-7-[4-(4-cyanophenyl)-4-{[1-(tert-butyl)-1,1-dimethylsilyl]oxy}butyl]-3,7-diazabicyclo[3.3.1]nonane-3-carboxylate Anhydrous potassium carbonate (0.96 g; 7 mmol) and tert-butyl-3,7-diazbicyclo[3.3.1]nonane-3-carboxylate (from step (v) above; 1.13 g; 5 mmol) were added to a stirred solution of 4-{[1-(tert-butyl)-1,1-dimethylsilyl]oxy}-4-(4-cyanophenyl)butyl methanesulfonate (from step (viii) above; 1.92 g; 5 mmol) in MeCN (5 mL) under an inert atmosphere ($N_2$). After addition was complete, the reaction was stirred at rt for 10 h. The solvent was evaporated and the residue partitioned between $CH_2Cl2$ and $NaHCO_3$ (aq.), then the organic layer was separated, dried and concentrated. Purification using column chromatography ($CH_2Cl_2$:MeOH; 19:1) gave the title compound in 96% yield.

(x) tert-Butyl 7-[4-(4-cyanophenyl)-4-hydroxybutyl]-3,7-diazabicyclo-[3.3.1]nonane-3-carboxylate Tetrabutylammonium fluoride (0.95 mmol) was added to a stirred solution of tert-butyl 7-[4-(4-cyanophenyl)-4-{[1-

(tert-butyl)-1,1-dimethylsilyl]-oxy}butyl]-3,7-diazabicyclo[3.3.1]nonane-3-carboxylate (from step (ix) above; 0.44 g; 0.85 mmol) in THF (5 mL), and the reaction mixture stirred at rt for 2 h. The solvent was then evaporated and the residue subjected to column chromatography (MeCN:MeOH; gradient 0–10% MeOH) to give the title compound in 70% yield.

ESI-MS: m/z=400.0 (M+H$^+$); $^{13}$C NMR in CDCl$_3$: δ 22.26, 28.37, 30.10, 37.26, 37.63, 47.68, 48.53, 57.73, 58.34, 59.12, 72.49, 78.95, 110.03, 119.05, 126.59, 131.71, 151.05, 155.58

(xi) tert-Butyl 7-[4-(4-cyanophenyl)-4-(3,4-dimethoxyphenoxy)butyl]-3,7-diazabicyclo[3.3.1]nonane-3-carboxylate Triphenylphosphine (1.11 g; 4.25 mmol) in 5 mL CH$_2$Cl$_2$ and 1,1'-(azodicarbonyl)dipiperidine (1.07 g; 4.25 mmol) in 15 mL CH$_2$Cl$_2$ were added to a stirred solution of 3,4-dimethoxyphenol (0.65 g; 4.25 mmol) and tert-butyl 7-[4-(4-cyanophenyl)-4-hydroxybutyl]-3,7-diazabicyclo-[3.3.1]nonane-3-carboxylate (from step (x) above; 0.85 g; 2.12 mmol). After 3 h, the precipitate was filtered off, and the filtrate concentrated. The residue was dissolved in aqueous tartaric acid (1 M; 25 mL) and the solution was washed with diethyl ether. The aqueous phase was made basic with and extracted again with diethyl ether. The organic layer from this second extraction was separated, dried (Na$_2$SO$_4$) and then concentrated to give the title compound in 21% yield.

Example 2 tert-Butyl 7-[4-(4-cyanophenyl)-4-(4-hydroxyphenoxy)butyl]-3,7-diazabicyclo [3.3.1] nonane-3-carboxylate (i) 4-{1-[4-(Tetrahydro-2H-pyran-2-yloxy)phenoxy]-3-butenyl}benzonitrile 4-(Tetrahydro-2H-pyran-2-yloxy)phenol (19.0 g; 0.1 mol) and 4-(1-hydroxy-3-butenyl)benzonitrile (17.8 g; 0.1 mol) was mixed in toluene, and cooled to 0° C. (under nitrogen). TBP (22.9 g; 0.11 mol) was added, followed by ADDP. The mixture was stirred at rt overnight, filtered, and evaporated. Purification by chromatography on silica gave 24 g (68.7%) of the desired compound.

(ii) 4-{4-Hydroxy-1-[4-(tetrahydro-2H-pyran-2-yloxy)phenoxy]butyl}benzonitrile

4-{1-[4-(Tetrahydro-2H-pyran-2-yloxy)phenoxy]-3-butenyl}benzonitrile (from step (i) above; 4.6 g; 13 mmol) was dissolved in dry THF (50 mL) under argon and cooled to −5° C. Borane-methylsulfide complex (BH$_3$xSMe$_2$) (3.5 mL of a 2 M solution in ether) was added dropwise at 0 to 5° C. The mixture was stirred at that temperature for 1.5 h. After 4 h at rt, tlc showed that the reaction was complete. The reaction mixture was quenched with 14 mL of H$_2$O and 5 g of NaBO$_3$. The mixture was stirred overnight, the solvent decanted off, and the residue treated with ether and decanted. The combined organic fractions were washed with brine, dried (Na$_2$SO$_4$), and evaporated. The crude product was purified by chromatography on silica (iso-propanol:ethyl acetate:heptane; 5:20:70). Yield: 2.44 g (58%).

(iii) 4-(4-Cyanophenyl)-4-[4-(tetrahydro-2H-pyran-2-yloxy)phenoxy]butyl Methanesulfonate The sub-title compound was prepared in quantitative yield from 4-{4-hydroxy-1-[4-(tetrahydro-2H-pyran-2-yloxy)phenoxy]butyl}benzonitrile (from step (ii) above) according to the procedure described in Example 1 (viii) above.

(iv) tert-Butyl 7-{4-(4-cyanophenyl)-4-[4-(tetrahydro-2H-pyran-2-yloxy)-phenoxy]butyl}-3,7-diazabicyclo[3.3.1]nonane-3-carboxylate The sub-title compound was prepared in 75% yield from 4-(4-cyanophenyl)-4-[4-(tetrahydro-2H-pyran-2-yloxy)phenoxy]butyl methane-sulfonate (from step (iii) above) and tert-butyl 3,7-diazabicyclo[3.3.1]nonane (see Example 1(v) above) according to the method described in Example 1 (ix) above.

(v) tert-Butyl 7-[4-(4-cyanophenyl)-4-(4-hydroxyphenoxy)butyl]-3,7-diaza-bicyclo[3.3.1.]nonane-3-carboxylate tert-Butyl 7-{4-(4-cyanophenyl)-4-[4-(tetrahydro-2H-pyran-2-yloxy)-phenoxy]butyl}-3,7-diazabicyclo[3.3.1]nonane-3-carboxylate (from step (iv) above; 2.33 g; 4.0 mmol), was dissolved in THF (40 mL), acetic acid (20 mL) and H$_2$O (10 mL). The mixture was stirred at 35° C. for 2 days. The mixture was made basic with 10 M NaOH (whilst cooling). Extraction with DCM, separation of the organic layer, evaporation of the solvent and chromatography on silica (CH$_3$CN) gave 1.43 g (72%) of the title compound.

ESI-MS: m/z=492.1 (MH$^+$); $^{13}$C NMR in CDCl$_3$: δ 22.66, 28.55, 28.88, 29.19, 31.51, 35.50, 35.77, 47.79, 48.88, 57.70, 57.88, 58.69, 58.78, 59.54, 78.93, 80.12, 110.97, 115.97, 117.03, 118.78, 126.97, 132.24, 147.80, 150.80, 151.27, 155.34

Example 3 tert-Butyl 7-[4-(4-cyanophenyl)-4-(4-pyridinylmethoxy)butyl]-3,7-diaza-bicyclo[3.3.1]nonane-3-carboxylate NaH (0.059 g; 55% suspension in oil; 1.35 mmol) was washed with petroleum ether (fraction 40/60). 2 mL of DMSO was added. tert-Butyl 7-[4-(4-cyanophenyl)-4-hydroxybutyl]-3,7-diazabicyclo[3.3.1]nonane-3-carboxylate (see Example 1(x) above; 0.54 g; 1.05 mmol) dissolved in 10 mL of DMF was added dropwise at 0° C. After 15 minutes, 4-pyridinylmethyl chloride (0.17 g; 1.05 mmol) was added dropwise at 0° C. The mixture was stirred at 0° C. for 30 minutes, then at rt overnight. The reaction mixture was diluted with water and extracted with ethyl acetate:toluene (1:1). The organic layer was separated and washed with brine and water. Evaporation in vacuo gave 0.56 g of crude product. Purification on silica (DCM:10% MeOH) gave 0.17 g (26%) of the title compound.

ESI-MS: m/z=491.0 (MH$^+$); $^{13}$C NMR in CDCl$_3$: δ 22.35, 28.38, 28.74, 28.95, 31.25, 35.10, 47.51, 48.58, 57.89, 58.50, 59.08, 59.22, 68.92, 78.24, 81.42, 81.55, 111.26, 118.57, 121.52, 127.75, 132.19, 147.12, 147.47, 149.57, 154.86

Example 4

The title compounds of Examples 1 to 3 above were tested in Test A above and were found to exhibit D$_{10}$ values of more than 6.0.

| Abbreviations | |
|---|---|
| ADDP = | 1,1'-(azodicarbonyl)dipiperidine |
| aq. = | aqueous |
| atm. = | atmospheres |
| DMF = | dimethylformamide |
| DMSO = | dimethylsulfoxide |
| Et = | ethyl |
| EtOAc = | ethyl acetate |
| ESI = | electron spray interface |
| FAB = | fast atom bombardment |
| h = | hours |
| IPA = | iso-propanol |
| LC = | liquid chromatography |
| HPLC = | high performance liquid chromatography |

-continued

| Abbreviations | |
|---|---|
| Me = | methyl |
| MeCN = | acetonitrile |
| MeOH = | methanol |
| min. = | minutes |
| MS = | mass spectroscopy |
| NADPH = | nicotinamide adenine dinucleotide phosphate, reduced form |
| NMR = | nuclear magnetic resonance |
| Pd/C = | palladium on carbon |
| rt. = | room temperature |
| sat. = | saturated |
| TBP = | tributyl phosphine |
| THF = | tetrahydrofuran |
| tlc = | thin layer chromatography |

Prefixes n, s, i and t have their usual meanings: normal, iso, secondary and tertiary.

What is claimed is:

1. A compound of formula I,

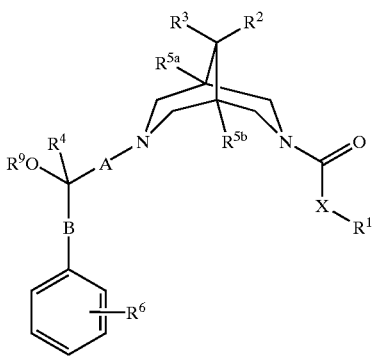

wherein $R^1$ represents $C_{1-12}$ alkyl, —$(CH_2)_a$-aryl, or —$(CH_2)_a$-$Het^1$ (all of which are optionally substituted and/or terminated (as appropriate) by one or more substituents selected from —OH, halo, cyano, nitro, $C_{1-4}$ alkyl and/or $C_{1-4}$ alkoxy);

represents 0, 1, 2, 3, or 4;

$Het^1$ represents a five to ten-membered heterocyclic ring containing one or more heteroatoms selected from oxygen, nitrogen and/or sulfur, and which also optionally includes one or more =O substituents;

X represents O or S;

$R^{5a}$ and $R^{5b}$ independently represent H or $C_{1-3}$ alkyl;

$R^2$ and $R^3$ independently represent H, $C_{1-4}$ alkyl (optionally substituted and/or terminated with one or more nitro or cyano groups), $OR^7$, $N(R^{7a})R^{7b}$, $OC(O)R^8$ or together form —O—$(CH_2)_2$—O—, —$(CH_2)_3$—, —$(CH_2)_4$— or —$(CH_2)_5$—;

$R^7$ and $R^8$ independently represent H, $C_{1-6}$ alkyl or —$(CH_2)_b$-aryl (which latter two groups are optionally substituted and/or terminated by one or more substituents selected from —OH, halo, cyano, nitro, $C_{1-4}$ alkyl and/or $C_{1-4}$ alkoxy);

$R^{7a}$ and $R^{7b}$ independently represent H or $C_{1-6}$ alkyl;

b represents 0, 1, 2, 3 or 4;

$R^4$ represents H or $C_{1-6}$ alkyl;

$R^9$ represents —$C(O)R^{10}$, $C_{1-6}$ alkyl, —$(CH_2)_d$-aryl or —$(CH_2)_d$-$Het^2$ (which latter three groups are optionally substituted by one or more substituents selected from —OH, halo, cyano, nitro, $C_{1-4}$ alkyl, $C_{1-4}$ alkoxy, $C(O)R^{11}$, $C(O)OR^{12}$ and/or —$N(H)S(O)_eR^3$);

$R^{10}$, $R^{11}$ and $R^{12}$ independently represent H, $C_{1-6}$ alkyl, $Het^3$ or —$(CH_2)_f$-aryl (which latter three groups are optionally substituted and/or terminated (as appropriate) by one or more substituents selected from —OH, cyano, halo, amino, nitro, $C_{1-6}$ alkyl, $C_{1-6}$ alkoxy, $C(O)R^{14}$, $C(O)OR^{15}$ and/or $N(H)S(O)_2R^{16}$);

$R^{13}$ represents $C_{1-6}$ alkyl or —$(CH_2)_g$-aryl (both of which are optionally substituted and/or terminated (as appropriate) by one or more substituents selected from halo, nitro, $C_{1-6}$ alkyl and/or $C_{1-6}$ alkoxy); $R^{14}$ and $R^{15}$ independently represent H, $C_{1-6}$ alkyl or aryl; $R^{16}$ represents $C_{1-6}$ alkyl or aryl;

e represents 0, 1 or 2;

d, f and g independently represent 0, 1, 2, 3 or 4;

$Het^2$ and $Het^3$ independently represent five to ten-membered heterocyclic rings containing one or more heteroatoms selected from oxygen, nitrogen and/or sulfur, and which also optionally includes one or more =O substituents;

$R^6$ represents one or more optional substituents selected from —OH, cyano, halo, amino, nitro, $C_{1-6}$ alkyl (optionally terminated by $N(H)C(O)OR^{18}$), $C_{1-6}$ alkoxy, —$C(O)N(H)R^{19}$, —$NHC(O)N(H)R^{20}$, —$N(H)S(O)_2R^{21}$ and/or —$OS(O)_2R^{22}$;

$R^{19}$ and $R^{20}$ independently represent H or $C_{1-6}$ alkyl;

$R^{18a}$, $R^{21}$ and $R^{22}$ independently represent $C_{1-6}$ alkyl;

A represents a single bond, $C_{1-6}$ alkylene or —$(CH_2)_j$C(H)($OR^{23}$)($CH_2$)$_k$— (in which latter group, the —$(CH_2)_j$— group is attached to the bispidine nitrogen atom and which latter two groups are optionally substituted by one or more —OH groups);

B represents a single bond, $C_{1-4}$ alkylene, —$(CH_2)_mN(R^{24})$—, —$(CH_2)_mS(O)_n$—, —$(CH_2)_mO$— (in which three latter groups, the —$(CH_2)_m$— group is attached to the carbon atom bearing $OR^9$ and $R^4$), —$C(O)N(R^{24})$— (in which latter group, the —$C(O)$— group is attached to the carbon atom bearing $OR^9$ and $R^4$), —$N(R^{24})C(O)O(CH_2)_m$— or —$N(R^{24})(CH_2)_m$— (in which latter two groups, the $N(R^{24})$ group is attached to the carbon atom bearing $OR^9$ and $R^4$);

j represents 1, 2, 3 or 4;

k and m independently represent 0, 1, 2, 3 or 4;

n represents 0, 1 or 2;

$R^{23}$ represents H, $C_{1-6}$ alkyl or $C(O)R^{25}$;

$R^{24}$ represents H or $C_{1-6}$ alkyl;

$R^{25}$ represents H, $C_{1-6}$ alkyl, $Het^4$ or —$(CH_2)_p$-aryl (which latter two groups are optionally substituted and/or terminated (as appropriate) by one or more substituents selected from —OH, cyano, halo, amino, nitro, $C_{1-6}$ alkyl and/or $C_{1-6}$ alkoxy);

$Het^4$ represents a five to ten-membered heterocyclic ring containing one or more heteroatoms selected from oxygen, nitrogen and/or sulfur, and which also optionally includes one or more =O substituents; p represents 0, 1, 2, 3 or 4;

or a pharmaceutically acceptable derivative thereof;

provided that m does not represent 0 when B represents —$(CH_2)_mN(R^{24})$—, —$(CH_2)_mS(O)_n$— or —$(CH_2)_mO$—.

2. A compound as claimed in claim 1, wherein $R^1$ represents optionally substituted —$(CH_2)_a$-phenyl, in which a is 0, 1, 2 or 3, or optionally substituted, optionally unsaturated, linear, branched or cyclic, $C_{1-8}$ alkyl (which latter group may also be interrupted by an oxygen atom).

3. A compound as claimed in claim 1, wherein $R^2$ represents H.

4. A compound as claimed in claim 1, wherein $R^3$ represents H.

5. A compound as claimed in claim 1, wherein $R^4$ represents H or $C_{1-2}$ alkyl.

6. A compound as claimed in claim 1, wherein $R^{5a}$ and $R^{5b}$ either both represent H or both represent methyl.

7. A compound as claimed in claim 1, wherein $R^6$ represents one or more substituents selected from $C_{1-6}$ alkyl, cyano, nitro, amino, $C(O)N(H)R^{19}$ and/or —$N(H)S(O)_2R^{21}$.

8. A compound as claimed in claim 1, wherein X represents O.

9. A compound as claimed in claim 1, wherein A represents a single bond or linear, or branched, $C_{1-6}$ alkylene (which group is also optionally interrupted by O).

10. A compound as claimed in claim 1, wherein B represents a single bond, $C_{1-4}$ alkylene, —$(CH_2)_mO$— or —$(CH_2)_mN(R^{24})$— (in which latter two cases m is 1, 2 or 3).

11. A compound as claimed in claim 1, wherein $R^9$ represents $C(O)R^{10}$ (in which $R^{10}$ represents $C_{1-3}$ alkyl or optionally substituted $Het^3$); $C_{1-3}$ alkyl; optionally substituted phenyl; or optionally substituted —$(CH_2)_d$-$Het^2$ (in which d is 0, 1 or 2).

12. A pharmaceutical formulation including a compound as defined in claim 1 in admixture with a pharmaceutically-acceptable adjuvant, diluent or carrier.

13. A pharmaceutical formulation for use in the prophylaxis or the treatment of an arrhythmia, comprising a compound as defined in claim 1.

14. A compound as defined in claim 1 for use as a pharmaceutical.

15. A compound as defined in claim 1 for use in the prophylaxis or the treatment of an arrhythmia.

16. The use of a compound as defined in claim 1 as active ingredient in the manufacture of a medicament for use in the prophylaxis or the treatment of an arrhythmia.

17. The use as claimed in claim 16, wherein the arrhythmia is an atrial or a ventricular arrhythmia.

18. A method of prophylaxis or treatment of an arrhythmia which method comprises administration of, a therapeutically effective amount of a compound as defined in claim 1 to a person suffering from, or susceptible to, such a condition.

19. A process for the preparation of a compound of formula I as defined in claim 1 which comprises:

(a) reaction of a compound of formula II,

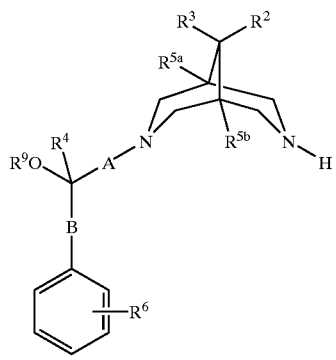

II wherein $R^2$, $R^3$, $R^4$, $R^{5a}$, $R^{5b}$, $R^6$, $R^9$, A and B are as defined in claim 1 with a compound of formula III, $$R^1XC(O)L^1 \quad \text{III}$$

wherein $L^1$ represents a leaving group and $R^1$ and X are as defined in claim 1;

(b) reaction of a compound of formula IV

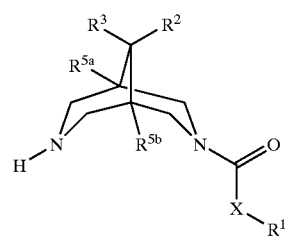

IV wherein $R^1$, $R^2$, $R^3$, $R^{5a}$, $R^{5b}$ and X are as defined in claim 1, with a compound of formula V,

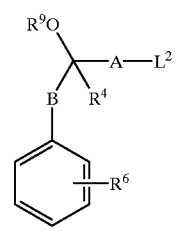

V wherein $L^2$ represents a leaving group and $R^4$, $R^6$, $R^9$, A and B are as defined in claim 1;

(c) for compounds of formula I in which one of $R^2$ and $R^3$ represents H or OH and the other represents H, reduction of a corresponding compound of formula VI,

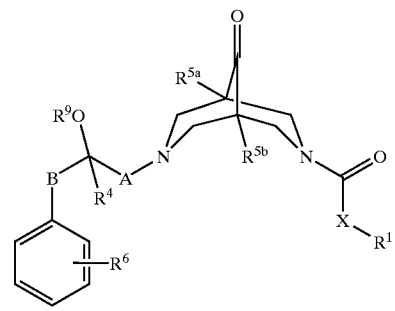

VI wherein $R^1$, $R^4$, $R^{5a}$, $R^{5b}$, $R^6$, $R^9$, A, B and X are as defined in claim 1;

(d) for compounds of formula I in which $R^9$ represents optionally substituted $C_{1-6}$ alkyl, optionally substituted —$(CH_2)_d$-aryl or optionally substituted —$(CH_2)_d$-$Het^2$, reaction of a compound of formula VII,

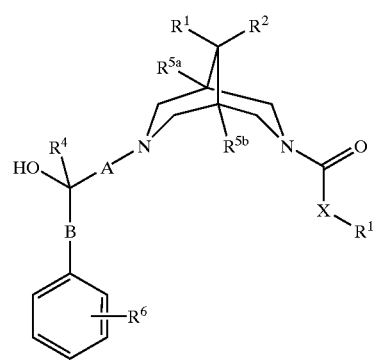

VII wherein $R^1$, $R^2$, $R^3$, $R^4$, $R^{5a}$, $R^{5b}$, $R^6$, A, B and X are as defined in claim 1 with a compound of formula VIII, $$R^{9a}OH \quad \text{VIII}$$

wherein $R^{9a}$ represents optionally substituted $C_{1-6}$ alkyl, optionally substituted $—(CH_2)_d$-aryl or optionally substituted $—(CH_2)_d$-Het$^2$ and d and Het$^2$ are as defined in claim 1;

(e) for compounds of formula I in which $R^9$ represents optionally substituted $C_{1-6}$ alkyl, optionally substituted $—(CH_2)_d$-aryl or optionally substituted $—(CH_2)_d$-Het$^2$, reaction of a compound of formula IX,

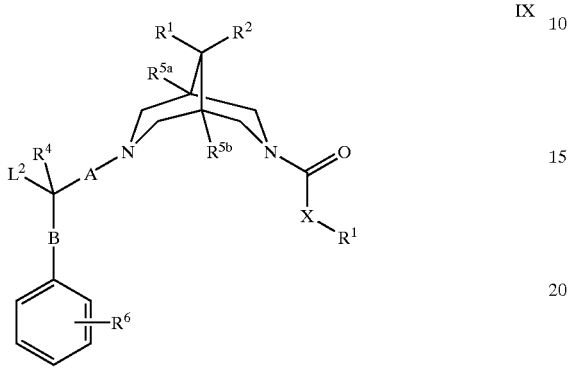

IX wherein $L^2$ is as defined above and $R^1$, $R^2$, $R^3$, $R^4$, $R^{5a}$, $R^{5b}$, $R^6$, A, B and X are as defined in claim 1 with a compound of formula VIII as defined above;

(f) for compounds of formula I in which $R^9$ represents $C(O)R^{10}$ and $R^{10}$ is as defined in claim 1, reaction of a corresponding compound of formula VII as defined above with a compound of formula X, $R^{10}CO_2H$      X wherein $R^{10}$ is as defined in claim 1;

(g) for compounds of formula I in which $R^2$ and/or $R^3$ represent $OC(O)R^8$ and $R^8$ is as defined in claim 1, coupling of a corresponding compound of formula I in which $R^2$ and/or $R^3$ (as appropriate) represents OH and a compound of formula XI, $R^8CO_2H$      XI wherein $R^8$ is as defined in claim 1;

(h) for compounds of formula I which are bispidine-nitrogen N-oxide derivatives, oxidation of the corresponding bispidine nitrogen of a corresponding compound of formula I;

(i) for compounds of formula I which are $C_{1-4}$ alkyl quaternary ammonium salt derivatives, in which the alkyl group is attached to a bispidine nitrogen, reaction, at the bispidine nitrogen, of a corresponding compound of formula I with a compound of formula XII, $R^x$Hal      XII wherein $R^x$ represents $C_{1-4}$ alkyl and Hal represents Cl, Br or I;

(j) reaction of a compound of formula II, as defined above, with a compound of formula XIII, $R^1XH$      XIII wherein $R^1$ and X are as defined in claim 1, in the presence of 1,1'-carbonyldiimidazole;

(k) for compounds of formula I in which one or both of $R^2$ and $R^3$ represent $—N(R^{7a})R^{7b}$ in which one or both or $R^{7a}$ and $R^{7b}$ represents $C_{1-6}$ alkyl, alkylation of a corresponding compound of formula I in which $R^2$ and/or $R^3$ represent $—N(R^{7a})R^{7b}$ (as appropriate) in which $R^{7a}$ and/or $R^{7b}$ (as appropriate) represent H, using a compound of formula XIIIA, $R^{7c}L^1$      XIIIA wherein $R^{7c}$ represents $C_{1-6}$ alkyl and $L^1$ is as defined above;

(l) conversion of one $R^6$ substituent to another; or (m) deprotection of a protected derivative of a compound of formula I as defined in claim 1.

* * * * *

UNITED STATES PATENT AND TRADEMARK OFFICE
CERTIFICATE OF CORRECTION

PATENT NO. : 6,465,481 B1  
DATED : October 15, 2002  
INVENTOR(S) : Frantsi et al.

It is certified that error appears in the above-identified patent and that said Letters Patent is hereby corrected as shown below:

Column 1,  
Line 49, please change "ye European" to -- European --.  
Line 50, please change "655 228" to -- 665 228 --.

Column 2,  
Line 38, please change "sub stituents" to -- substituents --.  
Lines 43-44, please change "OC(O)RS" to -- $OCOR^8$ --.

Column 5,  
Line 37, please change "$C_{13}$ alkyl" to -- $C_{1-3}$ alkyl --.  
Line 45, please change "$C_2$alkyl" to -- $C_{2-6}$ alkyl --.  
Line 65, please change "in vention" to -- invention --.

Column 8,  
Line 4, please change "-$(CH_2)_d$-HeO" to -- $(CH_2)_d$-$Het^2$ --.  
Line 48, please change "temperature i" to -- temperature --.

Column 18,  
Line 60, please change "$CH_2Cl2$" to -- $CH_2Cl_2$ --.

Column 21,  
Line 43, please change "represents" to -- a represents --.

Column 23,  
Line 40, please change "of,a" to -- of a --.

Signed and Sealed this

Nineteenth Day of August, 2003

JAMES E. ROGAN  
*Director of the United States Patent and Trademark Office*